United States Patent [19]
Chaudhuri et al.

[11] Patent Number: 6,143,794
[45] Date of Patent: Nov. 7, 2000

[54] TOPICAL FORMULATIONS FOR THE TREATMENT OF NAIL FUNGAL DISEASES

[75] Inventors: Bhaskar Chaudhuri, Cupertino; Ming Fai Chim, San Francisco; Daniel Bucks, Millbrae, all of Calif.

[73] Assignee: Bertek Pharmaceuticals, Inc., Foster City, Calif.

[21] Appl. No.: 09/289,205

[22] Filed: Apr. 9, 1999

Related U.S. Application Data

[60] Provisional application No. 60/082,187, Apr. 17, 1998.

[51] Int. Cl.[7] .......................... A61K 31/13; A61K 31/135
[52] U.S. Cl. ............................................................. 514/655
[58] Field of Search ............................................. 514/655

[56] References Cited

U.S. PATENT DOCUMENTS

| | | | |
|---|---|---|---|
| 4,079,028 | 3/1978 | Emmons et al. | 260/29.6 |
| 4,155,892 | 5/1979 | Emmons et al. | 240/29.2 |
| 4,746,509 | 5/1988 | Haggiage et al. | 424/449 |
| 4,822,822 | 4/1989 | Arita et al. | 514/655 |
| 4,957,730 | 9/1990 | Bohn et al. | 424/61 |
| 4,962,178 | 10/1990 | Harisiades | 528/33 |
| 4,971,800 | 11/1990 | Chess et al. | 424/449 |
| 5,002,938 | 3/1991 | Wang et al. | 514/171 |
| 5,021,458 | 6/1991 | Maeda et al. | 514/655 |
| 5,045,317 | 9/1991 | Chess et al. | 424/401 |
| 5,051,260 | 9/1991 | Chess et al. | 424/449 |
| 5,106,866 | 4/1992 | Maeda et al. | 514/443 |
| 5,286,787 | 2/1994 | Podola et al. | 524/773 |
| 5,322,685 | 6/1994 | Nakagawa et al. | 424/78.03 |
| 5,334,628 | 8/1994 | Maeda et al. | 514/311 |
| 5,639,740 | 6/1997 | Crandall | 514/78 |
| 5,696,164 | 12/1997 | Sun et al. | 514/562 |
| 5,916,545 | 6/1999 | Burnett et al. | 424/61 |

FOREIGN PATENT DOCUMENTS

| | | |
|---|---|---|
| 1 175 355 | 10/1984 | Canada . |
| 0 055 397 B1 | 8/1984 | European Pat. Off. . |
| 0 440 298 A1 | 8/1991 | European Pat. Off. . |
| 196 04 190 A1 | 8/1997 | Germany . |
| 2 202 743 | 10/1988 | United Kingdom . |
| WO 93/11735 | 6/1993 | WIPO . |
| WO 96/19186 | 6/1996 | WIPO . |

OTHER PUBLICATIONS

Hisamitsu Pharmaceutical Co., Inc., "JP 07 206711: Composition for Treatment of Trichophytosis Unguium," Patent abstracts of Japan, vol. 095, No. 011, Dec. 26, 1995.

Hisamitsu Pharmaceutical Co., Inc., "JP 06 211651: Composition for Treatment Nail Trichophytosis," Patent Abstracts of Japan, vol. 018, No. 575, Nov. 04, 1994.

Miyata et al, "External Preparation for Nail Ringworm," Chemcial Abstracts, vol. 125, No. 6, Abstract No. 67762, 1996.

Syed et al., "Management of Toenail Onychomycosis with 2% Butenafine and 20% Urea Cream: A Placebo–controlled, Double–blind Study," Journal of Dermatology, vol. 25, pp. 648–652, 1998.

Meyerson, "Open–label Study of the Safety and Efficacy of Naftifine Hydrochloride 1 Percent Gel in Patients with Distal Subungual Onychomychosis of the Fingers", Therapeutics for the Clinician, vol. 51, pp. 205–207, Mar. 1993.

Saunders, "Polyurethanes: Chemistry and Technology, vol. 16, pp. 65–67, Interscience Publishers", 1962.

*Primary Examiner*—Theodore J. Criares
*Assistant Examiner*—Jennifer Kim
*Attorney, Agent, or Firm*—Cooley Godward LLP

[57] ABSTRACT

Stable, topical formulations useful for treating a nail fungal disease are disclosed. The compositions comprise an antifungal compound and at least one pharmaceutically acceptable excipient sufficient to form a gel. The antifungal compound is represented by the formula

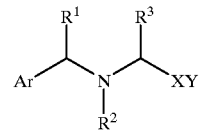

where $R^1$, $R^2$, and $R^3$ are independently hydrogen or lower alkyl; X is —$(CH_2)_n$— in which n is 0, 1 or 2; Y is aryl or heteroaryl; and Ar is aryl or heteroaryl. The composition is applied to the afflicted nail for once a day until the fungal disease is cured.

22 Claims, No Drawings

TOPICAL FORMULATIONS FOR THE TREATMENT OF NAIL FUNGAL DISEASES

This application claims the benefit of U.S. Provisional Application No. 60/082187, filed Apr. 17, 1998.

TECHNICAL FIELD

The invention relates to stable topical formulations useful for the treatment of nail fungal diseases and a method of treating fungal diseases in nails.

BACKGROUND

Many methods are known for the treatment of fungal infections, including the oral and topical use of antibiotics (e.g. nystatin and amphotericin B), imidazole antifungal agents such as miconazole, clotrimazole, fluconazole, econazole and sulconazole, and non-imidazole fungal agents such as the allylamine derivatives terbinafine and naftifine, and the benzylamine butenafine.

Onychomycosis is a fungal infection of the nail unit caused by yeast, dermatophytes, or other molds, and represents approximately 50% of all nail disorders. Toenail infection accounts for approximately 80% of onychomycosis incidence, while fingernails are affected in about 20% of the cases. Dermatophytes are the most frequent cause of nail plate invasion, particularly in toenail onychomycosis. Onychomycosis caused by a dermatophyte is termed tinea unguium. *Trichophyton rubrum* is by far the most frequently isolated dermatophyte, followed by *T. mentagrophytes*. Distal subungual onychomycosis is the most common presentation of tinea unguium, with the main site of entry through the hyponychium, progressing in time to involve the nail bed and the nail plate. The disease is characterized by discoloration, onycholysis, accumulation of subungual debris and nail plate dystrophy. Diagnosis can be confirmed by KOH (potassium hydroxide) preparations and mycologic culture. The disease adversely affects the quality of life of its victims, with subject complaints ranging from unsightly nails and discomfort with footwear, to more serious complications including secondary bacterial infections.

Onychomycosis has proved to be resistant to treatment. Nail fungal infections reside in an area difficult to access by conventional topical treatment, and antifungal drugs cannot readily penetrate the nail plate to reach the infection sites under the nail. Therefore, onychomycosis has traditionally been treated by oral administration of antifungal drugs; however, clearly this is undesirable due to the potential for side effects of such drugs, in particular those caused by the more potent antifungal drugs such as itraconazole and ketoconazole. An alternative method of treatment of onychomycosis is by removal of the nail before treating with a topically active antifungal agent; such a method of treatment is equally undesirable.

Onychomycoses do not resolve spontaneously, and even if successfully treated, tend to recur. Treatment of onychomycosis is often a challenging endeavor for the clinician. Systemic antimycotic agents require prolonged use and have the potential for significant side effects. Topical agents have usually been of little benefit.

It would therefore be advantageous to have a topical formulation that is capable of penetrating the nail barrier and effectively treating nail fungal diseases, thus avoiding oral administration of antifungal drugs and the necessity of removing the nail. It would be preferable if such treatment required only nightly applications of the formulation, i.e. effective treatment did not require that the formulation be resident 24 hours per day on the nails over a long period of time. This patent application describes such a formulation.

Publications of interest are WO 96/19186, U.S. Pat. No. 4,746,509, U.S. Pat. No. 4,822,822, U.S. Pat. No. 5,322,685, PCT Application US92/10989, EP Patent Application 55,397, GbB2, 202, 743A; and CA 1,175,355.

SUMMARY OF THE INVENTION

The present invention relates to a composition and a method for treating a fungal disease in a nail of a mammal, particularly a human. In particular, the invention relates to a stable topical formulation useful for the treatment of a nail fungal disease, comprising an antifungal agent and one or more pharmaceutically acceptable excipients sufficient to form a gel capable of delivering the antifungal through the nail barrier.

One aspect of the invention relates to a topical antifungal composition that comprises (a) an antifungal compound of the formula:

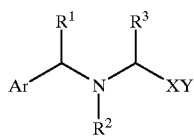

wherein:

$R^1$, $R^2$, and $R^3$ are independently hydrogen or lower alkyl;

X is —$(CH_2)_n$—, in which n is 0, 1 or 2;

Y is aryl or heteroaryl; and

Ar is aryl or heteroaryl, or a pharmaceutically acceptable salt thereof, in combination with (b) one or more pharmaceutical excipients sufficient to form a composition capable of adhering to the surface of the nail to deliver the antifungal through the nail barrier.

Another aspect of the invention is a method of treating a nail fungal disease by application to the nail of a mammal the claimed topical composition. The process comprises (a) applying a therapeutically-effective amount of the antifungal composition to the surface of the nail to be treated, (b) maintaining the composition on the nail for up to about 24 hours (preferably about 4 to about 12 hours), (c) removing the composition for a short time, preferably for about 4 to about 12 hours, and (d) repeating steps (a) through (c) until the fungal disease has been successfully treated.

Yet another aspect of the invention pertains to the use of the antifungal compound for the preparation of a topical composition for the treatment of a nail fungal disease, wherein a therapeutically-effective amount of the topical composition is (a) applied to the surface of the nail to be treated, (b) maintained on the nail for up to about 24 hours (preferably about 4 to about 12 hours), (c) removed for a short time, preferably for about 4 to about 12 hours, and (d) steps (a) through (c) are repeated until the fungal disease has been successfully treated.

Another aspect of the invention is an article of manufacture comprising the claimed topical composition in a container in combination with labeling instructions for application of the topical compositions in the treatment of nail fungal diseases.

Another aspect of the invention is an article of manufacture comprising the composition in combination with a covering device to retain the composition on the nail.

DETAILED DESCRIPTION AND PRESENTLY PREFERRED EMBODIMENTS

This invention is useful for topically treating onychomycosis, i.e. a flngal infection of the nail plate on the hands or feet of mammals, particularly humans. The nail fungal disease is usually caused by Epidermophyton, Microsporum, and/or Trichophyton and produces nails that are opaque, white, thickened, friable and brittle. Onychomycosis is sometimes called ringworm of the nails or tinea unguis. The composition delivers an antifungal compound to the nail plate (the stratum corneum unguis) and to the nail bed (the modified area of the epidermis beneath the nail, over which the nail plate slides as it grows) through the nail plate and around the nail periphery. Desirably the antifungal compound is also concurrently delivered to the nail matrix, the cuticle and the hyponychium (the thickened epidermis underneath the free distal end of a nail).

The invention has several aspects. One aspect is the composition itself. Another aspect is the use of the composition to treat onychomycosis. Still another aspect is, an article of manufacture, i.e., the composition in combination with printed labeling instructions explaining how to use the composition for the desired results. Still another aspect is an article of manufacture that comprises the combination of the composition with a covering adapted to retain the composition on the nail for an extended period of time.

Definitions

As used herein:

"Alkyl" means a branched or unbranched saturated monovalent hydrocarbon radical containing 1 to 12 carbon atoms, such as methyl, ethyl, propyl, isopropyl, tert-butyl, butyl, n-hexyl, dodecyl, and the like, unless otherwise indicated.

"Lower alkyl" means a branched or unbranched saturated monovalent hydrocarbon radical containing 1 to 6 carbon atoms, such as methyl, ethyl, propyl, isopropyl, tert-butyl, butyl, n-hexyl and the like, unless otherwise indicated.

"Lower alkoxy" means the group —O—(lower alkyl) wherein lower alkyl is as herein defined.

"Lower alkyl ethers of propylene glycol" refers to compounds of the formula (lower alkyl)—O—$CH_2$—$CH_2$($CH_3$)—O—(lower alkyl).

"Lower fatty acid esters of propylene glycol" refers to compounds of the formula (lower alkyl)—C(O)O—$CH_2$—$CH_2$($CH_3$)—OC(O)—(lower alkyl).

"Alkylene" means a branched or unbranched saturated divalent hydrocarbon radical containing 1 to 12 carbon atoms, such as methylene, ethylene, 1,2-propylene, 1,4-butylene, 1,3-butylene, 1,5-pentylene, 1,3-pentylene, 1,6-hexylene, 1,12-dodecylene, and the like.

"Alkenylene" means a branched or unbranched unsaturated divalent hydrocarbon radical containing 2 to 12 carbon atoms, such as ethene, 1-propene, 1-butene, 3-methylbut-1-ene, 1-pentene, 2-methylpent-1-ene, 1-hexene, 1-dodecene, and the like.

"Halo" means fluoro, chloro, bromo, or iodo.

The term "aryl" refers to a monovalent unsaturated aromatic carbocyclic radical having a single ring (e.g., phenyl) or two rings (e.g., naphthyl, biphenyl, indanyl, 1,2,3,4-tetrahydronaphthyl, benzocycloheptane), which can optionally be mono-, di- or tri-substituted, independently, with OH, COOH, lower alkyl, lower alkoxy, halo, nitro, amino, alkylamino, dialkylamino, trifluoromethyl and/or cyano.

The term "heteroaryl" refers to a monovalent aromatic carbocyclic radical having 1–3 heteroatoms within one or two rings, (e.g., thiophenyl, fuiranyl, pyridyl, thiazolyl, pyrimidine, oxazolyl, benzoxazole, benzofuran, benzothiophene, indolinyl, quinoline), which can optionally be mono-, di- or tri-substituted, independently, with OH, COOH, lower alkyl, lower alkoxy, halo, nitro, amino, alkylamino, dialkylamino, trifluoromethyl and/or cyano.

The term "heteroatom" refers to oxygen, sulfur or nitrogen, unless otherwise specified.

"Optional" or "optionally" means that the subsequently described event or circumstance may or may not occur, and that the description includes instances where said event or circumstance occurs and instances in which it does not. For example, "optionally substituted phenyl" or "optionally substituted naphthyl" means that the phenyl or naphthyl may or may not be mono-, di- or tri-substituted, independently, with OH, COOH, lower alkyl, lower alkoxy, halo, nitro, amino, and trifluoromethyl, and that the description includes both unsubstituted phenyl and naphthyl and substituted phenyl and naphthyl.

The term "pharmaceutically-acceptable" salt means a salt of an active compound that retains the biological effectiveness of the compound and that is not pharmacologically undesirable. A pharmaceutically-acceptable acid addition salt is one prepared from an organic or inorganic acid that pairs with an appropriate base, e.g., an amino group in the active compound. Inorganic salts derived are from inorganic acids such as hydrochloric acid, hydrobromic acid, sulfuric acid, nitric acid, phosphoric acid and the like. Organic salts are derived from acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, lactic acid and the like.

The Composition

Broadly, the composition comprises a therapeutically effective amount of an antifungal compound, or a pharmaceutically acceptable salt thereof, and at least one pharmaceutically acceptable excipient to provide a mixture having a consistency sufficient to adhere to the surface of a nail so that the antifungal is delivered through the nail plate. Generally the composition is a liquid or semisolid, such as a cream, ointment, lotion, or gel (preferably a gel) having a solvent in which the antifungal compound, or its salt, is dissolved. Thus, the composition will contain at least the antifungal compound, a solvent for the compound, and a gelling agent. Preferably, the composition is water-based, which means that the solvent is preferably water-miscible. In addition, the composition may include a surfactant to aid in the delivery of the antifungal through the nailplate; a keratolytic agent to aid in the loosening, disintegration or decomposition of the thickened nailplate; a film-forming agent; a buffering agent to adjust the pH of the composition; and an adherence-promoting agent to assist in adhering the composition to the nailplate. The composition may be applied directly to the nail or applied in an absorbent pad.

The antifungal compound useful in this invention is one that is effective when applied topically to treat the fungal infection. The amount of the compound present in the composition will be the amount that is therapeutically effective, i.e. an amount that will result in the effective treatment of the onychomycosis when applied in accordance with the instructions described herein. The term "treatment"

as used herein covers any treatment of onychomycosis in a mammal, particularly a human, and includes:

(i) preventing the disease from occurring in a subject which may be predisposed to the disease but has not yet been diagnosed as having it;

(ii) inhibiting the disease, i.e. arresting its development; and (iii) relieving the disease, i.e. causing regression of the disease.

The therapeutically effective amount will vary depending on the subject and the severity of the affliction and may be determined routinely by one of ordinary skill in the art in light of the teaching herein. Generally, a therapeutically effective amount will be from about one-half percent by weight (0.5% wt.) to about fifteen percent by weight (15% wt.) based on the total final weight of the composition. Preferably, the amount will be about 1% to about 10% by weight and more preferably about 2% to about 8% by weight. The amount present in the composition will be dependent in part on the length of the treatment, as discussed hereinafter.

The antifungal agents of particular utility in this invention have a structure represented by Formula (I), below, and the pharmaceutically-acceptable salts thereof. These include a benzylamine moiety (for example butenafine and related compounds are disclosed in U.S. Pat. Nos. 5,021,458 and 5,106,866). Each of the foregoing patents is incorporated by reference. Antifungal of particular interest include, but are not limited to, butenafine and the pharmaceutically-acceptable salts thereof. Such compounds are represented by Formula (I) as follows:

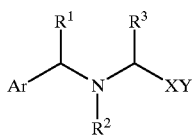

(I)

wherein Ar is aryl; $R^1$ is alkil or hydrogen; $R^2$ is hydrogen or alkyl, $R^3$ is hydrogen or alkyl; X is a covalent bond; and Y is aryl or heteroaryl.

Butenafine is a preferred compound of Formula I wherein Ar is 1-naphthyl, $R^1$ is hydrogen, $R^2$ is methyl, $R^3$ is hydrogen, X is —$(CH_2)_n$— in which n is 0, (i.e., a covalent bond) and Y is 4-(t-butyl)phenyl, and has the structure:

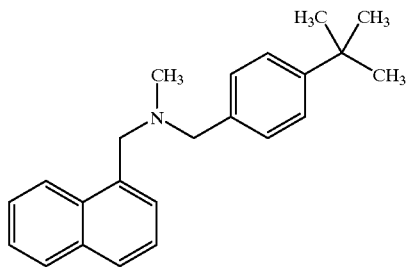

Of these compounds butenafine hydrochloride is preferred.

The pharmaceutically-acceptable solvent used in the composition of this invention is preferably miscible with water and will be present in an amount sufficient to dissolve the antifungal compound. Generally this amount will vary from about 20–80% by weight, preferably about 30% by weight to about 70% by weight, more preferably about 40% by weight to about 60% by weight. Examples of suitable solvents include pharmaceutically acceptable lower alkanols of one to four carbon atoms (e.g., ethanol, n-propanol, isopropanol, and n-butanol; preferably ethanol), pharmaceutically acceptable dihydroxylacohols (e.g., alkylene glycols such as hexylene glycol, propylene glycol, butylene glycol, and the like), benzylalcohol, propylene carbonate, polyethylene glycols (e.g., PEG 400), polypropylene glycols (e.g., PPG 725), and the like. Others may be apparent to one of ordinary skill upon reading this specification. Ethanol is preferred.

In addition to the antifungal compound and a pharmaceutically-acceptable solvent, the composition of this invention also includes a gelling agent in an amount sufficient to form a gel. Preferably the gel is a single-phase gel, i.e., it consists of organic macromolecules distributed throughout the composition in such a manner that no apparent boundaries exist between the dispersed macromolecules and the liquid. The gelling agent may be a synthetic macromolecule or a natural macromolecule, e.g., a gum, resin, polyacrylamide, mitrocellulose, or other cellulose derivatives. The gel is a semisolid preferably having a high degree of clarity, ease of application, and ease of removal. The amount of the gelling agent will vary depending on the type of solvent used, the type of gelling agent used to be appropriate with the solvent, and whether the system is aqueous or nonaqueous. Based on these considerations and others known to one of skill in the art, the gelling agent will be present in an amount from about 0.1% by weight to about 20% by weight, preferably about 0.5% by weight to about 15% by weight. Usually no more than about 10% by weight is used. Gels of this invention can be prepared from a number of pharmaceutical agents such as tragacanth about 2 to 5% wt., sodium alginate about 2 to 10% wt., gelatin about 2 to 15% wt., methylcellulose about 3 to 5% wt., sodium carboxymethylcellulose about 2 to 5% wt., carbomer about 0.3 to 5% wt., or polyvinyl alcohols about 10 to 20% wt. Other gelling agents include hydroxyethylmethyl cellulose, polyoxyethylene-polyoxypropylene block copolymers (polaxomers), ethylcellulose, and hydroxyethylcellulose. Preferably the gelling agent is chosen from methylcellulose, ethylcellulose, hydroxyethylcellulose, hydroxypropylcellulose, hydroxypropylmethylcellulose, carboxymethylcellulose and carbomer.

The gel composition of this invention is characterized by its ability to adhere to the nail being treated. Preferably, the composition will include a pharmaceutically-acceptable excipient to aid in improving adhesion properties. Certain polyurethane compounds provide superior adhesion properties and also aid in cutaneous penetration. Such a polyurethane compound would include any conventional polyurethane compound formed by reaction of a diisocyanate with a compound having an active hydrogen, for example as disclosed in U.S. Pat. No. 4,079,028 to Emmons, which is incorporated herein by reference. A compound having an active hydrogen includes alcohols, diols, triols, amines, hydroxy-terminated polyesters, silanols, carboxylic acids, and the like. More particularly, the polyurethane compound includes compounds having the formula:

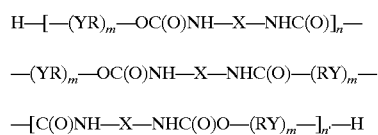

wherein:

X is an alkylene or alkenylene radical containing from 1 to about 20 carbon atoms, or a cycloalkylene or cycloalkenylene radical containing from about 5 to 20 carbon atoms, or a mononuclear or fused ring arylene radical containing from about 6 to about 10 carbon atoms, unsubstituted or substituted with one or more lower alkyl, lower alkoxy, lower alkoxy-substituted lower alkyl, nitro or arnino groups or halogen atoms;

Y is oxygen, sulfur, silicon, or —NH—;

each R is the same or different, and is chosen from alkylene, alkenylene, —SiR$^2$R$^3$—, and —CR$^2$R$^3$—NR$^4$—CR$^2$R$^3$—, wherein R$^2$, R$^3$ and R$^4$ are independently hydrogen or lower alkyl;

m is an integer selected to provide a (YR) moiety having a molecular weight of from about 40 to about 6,000; and n and n' are the same or a different integer from 0–30 inclusive, correlated with m so as to provide a polyurethane compound having a molecular weight of up to about 200,000. Polyurethane compounds where YR is —SiR$^2$R$^3$— or —CR$^2$R$^3$—NR$^4$—CR$^2$R$^3$— are well known in the art (See for example U.S. Pat. No. 5,286,787 to Padolo and Majolo; U.S. Pat. No. 4,962,178 to Harisiades; U.S. Pat. No. 4,155,892 to Emmons, et. al., and "Polyurethanes Chemistry and Technology" by J. H. Saunders and K. C. Frisch, Interscience Publishers, pp. 65–67.) Preferred are polyurethanes that are hydroxy-terminated polyurethanes, i.e. where Y is oxygen, especially those where R is alkylene or alkenylene, which are disclosed in U.S. Pat. Nos. 4,971,800, 5,045,317, and 5,051,260, the complete disclosures of which are hereby incorporated by reference. Also useful are those disclosed in U.S. Pat. 4,079,028 issued March 1978, to Emmons, et al. This, too, is incorporated herein by reference.

A preferred hydroxy-terminated polyurethane has the above formula where X is 4,4'-dicyclohexylmethane, Y is oxygen, R is 1,2-propylene, m is 1–4, n and n' are both 12. It has a tradename of polyolprepolymer-2, and is prepared by the reaction of 2 moles of polypropylene glycol and 1 mole of dicyclohexylmethane diisocyanate in the presence of stannous octoate, as detailed in U.S. Pat. No. 4,971,800, Examples 1 and 5. It has a CAS# 9042-82-4, and a CAS name poly[oxy(methyl-1,2-ethanediyl)], α-hydro-ω-hydroxy-, polymer with 1,1'-methylene-bis-[4-socyanatocyclohexane]. Also preferred is polyolprepolymer-14, which has the same CAS# and name, but a higher molecular weight (a weight average molecular weight of 14,000 as opposed to 4,000 for polyolprepolymer-2), and polyolprepolymer-15, which has a CAS# 39444-87-6, and is named poly(oxy-1,2-ethanediyl), α-hydro-ω-hydroxy-, polymer with 1,1'-methylene-bis-[4-isocyanatocyclohexane]. Generally, the optional adhesion-promoting agent will be present in an amount of 0% wt. to about 15%wt., preferably about 0.5% wt. to about 10% wt., and more preferably about 0.5% wt. to about 5% wt.

To further aid in retaining the gel composition of this invention on the surface of the nail, the composition may optionally include a film-forming agent in an amount sufficient to form a film on the surface of the gel exposed to air. Representative optional film forming agents include povidone (1-ethyenyl-2-pyrrolidone polymers, e.g., PVP K-90) polyvinyl alcohol, polyvinyl acetate, polyvinylethyl ether, polyvinyistearyl ether, vinylpyrrolidonel vinylacetate copolymers, nitrocellulose and the like. Generally, the optional film forming agent will be present in an amount of from 0% by wt. to about 5% by wt., preferably about 0.1% by wt. to about 3% by wt., more preferably about 0.1–2% by wt.

The gel composition of this invention may optionally include a surfactant to aid in the penetration of the antifungal compound through the nail plate. Representative surfactants include anionic and nonionic surfactants that are compatible with other components in the composition. Generally, the surfactant will be present in an amount of about 0% by wt to about 10% by wt., preferably about 0.5% wt to about 5% wt., more preferably about. to about 1% wt. to about 5% wt. Representatives examples of anionic surfactants include sodium lauryl sulfate, sodium laureth n-sulfate (where n is 5–12), sulfonates, sarcosinates, and sulfosuccinates. Nonionic surfactants include polysorbates, polyoxyethylene 4 lauryl ether, and the like.

The composition of this invention may optionally include a keratolytic agent, i.e., a desquamating agent, that loosen keratin in the nail and aids in the process of desquamation or the removal of the upper layers of the damaged or diseased nail. Examples of keratolytic agents include urea, benzoylperoxide, salicylic acid, resorcinol, tretinoin, and others that may be found in "Remington: The Science and Practice of Pharmacy, Nineteenth Edition, pp. 878–879. The optional keratytic agent will be present in an amount of 0% wt. to about 25% wt., preferably about 0% wt. to about 20% wt., more preferably about 1% wt. to about 20% wt.

Other excipients optionally present in the composition include a buffer for aqueous compositions to adjust the pH of the composition and a preservative. The pH will be non-irritating and is preferably adjusted to about 3.0–8.0 using an acid e.g. hydrochloric acid, phosphoric acid, lactic acid, or a base e.g. diethanolamine, triethanolamine, sodium hydroxide, or known buffering agents, e.g. phosphates such as monobasic sodium phosphate, and dibasic sodium phosphate, lactates and citrates well known in the art. A preservative may also be present, for example benzyl alcohol, sodium benzoate, methyl paraben, propyl paraben, and the like.

In summary, the gel formulation according to this invention exhibits a composition range shown in Table A.

TABLE A

| Component | Percent Weight | | |
| --- | --- | --- | --- |
| | Broad | Preferred | Most Preferred |
| Antifungal | 0.5–15 | 1–10 | 2–8 |
| Solvent | 20–80 | 30–70 | 40–60 |
| Gelling Agent | 0.1–20 | 0.5–15 | 0.5–10 |
| Adhesion-Promoting Agent | 0–15 | 0.5–10 | 0.5–5 |
| Film Forming Agent | 0–5 | 0.1–3 | 0.1–2 |
| Surfactant | 0–10 | 0.5–5 | 1–5 |
| Keratolytic Agent | 0–25 | 0–20 | 1–20 |
| Water | 0–qs | qs | qs |

The gel formulation according to this invention can also have a composition shown in Tables B and C.

TABLE B

| Ingredients | Wt % |
| --- | --- |
| Water | qs |
| Propylene glycol | 5–20 |
| Hydroxypropylcellulose | 1–5 |
| Ethanol | 20–80 |

TABLE B-continued

| Ingredients | Wt % |
| --- | --- |
| Polyolprepolymer-2 | 0–10 |
| Sodium laureth sulfate | 0–5 |
| Benzyl alcohol | 0–10 |
| Lactic acid | 0.1–1 |
| Sodium lactate | 1.5–15 |
| Povidone | 0–5 |
| Antifungal | 0.5–15 |

TABLE C

| Ingredients | Wt % |
| --- | --- |
| Water | qs |
| Propylene glycol | 5–15 |
| Hydroxypropylcellulose | 2–5 |
| Ethanol | 40–60 |
| Polyolprepolymer-2 | 0–3 |
| Sodium laureth sulfate | 0–3 |
| Benzyl alcohol | 0.5–5 |
| Lactic acid | 0.2–0.8 |
| Sodium lactate | 3–12 |
| Povidone | 0.2–1 |
| Antifungal | 1–10 |

A preferred gel formulation is shown in Table D.

TABLE D

| Ingredients | Wt % |
| --- | --- |
| Water | 19.86 |
| Propylene glycol | 10 |
| Hydroxypropylcellulose | 2 |
| Ethanol | 50 |
| Polyolprepolymer-2 | 1 |
| Sodium laureth sulfate | 1 |
| Benzyl alcohol | 1 |
| Lactic acid | 0.58 |
| Sodium lactate | 9.36 |
| Povidone | 0.2 |
| Butenafine HCl | 5 |

Another preferred gel formulation is shown in Table E.

TABLE E

| Ingredients | Wt % |
| --- | --- |
| Water | 21.83 |
| Propylene glycol | 10 |
| Hydroxypropylcellulose | 2 |
| Ethanol | 50 |
| Polyolprepolymer-2 | 1 |
| Sodium laureth sulfate | 1 |
| Benzyl alcohol | 1 |
| Lactic acid | 0.29 |
| Sodium lactate | 4.68 |
| Povidone | 0.2 |
| Butenafine HCl | 8 |

Treatment of Onychomycosis

Another aspect of this invention is a method for treating a nail fungus disease in a mammal. The method comprises
(a) applying a composition as discussed hereinbefore to the surface of the nail to be treated,
(b) maintaining the composition on a nail for at least up to about 24 hours, preferably about 4 to about 12 hours,
(c) removing the composition from the nail for a short time, about 4 to 12 hours, and
(d) repeating steps (a) through (c) until the nail fungus has been successfully treated.

This method of treatment may be used alone or in conjunction with other antifungal treatments. For example, at the same time a patient is being treated using the topical composition of this invention, he or she may also be taking oral antifungals to attack the disease systemically. While such a combination may be used, the composition of this invention is useful without any combination therapy.

In applying the composition to the nail, the entire surface of the nail is covered and the cuticle in the hyponychium will also be covered in whole or in part. Once the composition is applied to the nail area to be treated, depending on the type of composition it may be left alone to form a relatively stable gel composition that stays on the nail with a film forming on the surface if a film former is present. Optionally, the composition, once applied to the nail, is covered by a covering material that will aid in keeping the gel composition in place on the nail for the period of time desired. The covering may be occlusive or semi-occlusive, but will be of nature that will retain the composition on the nail. Thus, a simple bandage which has adhesive arms that will stick to the skin of a human finger or toe and has a covering area that will cover the entire nail is useful. Alternatively, the area designed to cover the nail may have a recessed portion into which a therapeutically effective amount of the composition is placed and the covering is then placed on the nail such that the portion of the composition retained in the depressed area is positioned directly on the nail so that the composition adheres to the surface of the nail. Such a combination can be adhered in place by having adhesive arms attached to it which will adhere to the skin or a piece of tape may simply be placed over the receptacle to ensure adhesion to the nail. The composition may be stored in a bottle or tube and applied by squeezing the composition onto the nail such as toothpaste is squeezed from a toothpaste tube or it may be brushed on to the nail using a brush and a suitable container. Alternatively, a prepackaged single application dose may also be used where the amount of for a single application to the nail is retained in a device having a recessed portion for the composition which can then be exposed to the nail and adhered to the finger or toe in which the nail is located.

Once the composition is on the nail it is retained there for an appropriate length of time that will depend on the concentration of the active ingredient in the composition and the individual patients' requirements. The composition may be kept on for a shorter period of time if a higher concentration of the active ingredient is employed and is kept on for a longer period of time if a lower concentration is used. Preferably, the composition will be maintained in contact with the nail for a period of time during which the patient is sleeping or inactive to avoid contact that might remove the composition from the nail. Thus, this will generally be up to about 24 hours, and usually about 4 to about 12 hours. Preferably a composition is kept on the nail for about 6 to 10 hours, more preferably about 8 hours. While it is conceivable that a regimen could be established wherein the composition is maintained in contact with the nail over an extended period of time, that is continuously, for example, for a week to a month, such a regimen would be somewhat difficult for a patient to adhere to. By continuous application in this case, it would mean that the composition would be removed from the nail only for a short period of time in order to replenish the material on the nail. Because most people are very active during the day, such an alternative treatment regimen is not likely to succeed. Thus, the preferred method is that the composition is removed from the nail for a period of about 4 to 12 hours and the composition is then re-applied and re-removed, repeating the process for a period of time which is long enough to successfully treat the nail fungus. The period of time in which this will be carried out may vary from a matter of about a week to a year or more depending on the degree of fungal involvement of the nail. A treatment regimen could include any number of possible regimens. For example, if a patient were treated by applying the composition to the surface of the nail and maintaining the composition for a 4 to 12 hour period using a high concentration of material with the next treatment being delayed for anywhere from 2 days to a week, it may take a year before effective treatment is obtained. If the patient receives a once a week treatment the final cure of the disease or elimination of the fungus may not be seen for more than a year or even up to five years. The treatments may be pulsed, e.g., one day on, three days off, one day on, etc. It is preferable to have a daily treatment which lasts for about 4 to 12 hours, followed by a period of time where there is no composition on the nail and then returning to the daily treatment. If this regimen is followed, generally at least a 12 week treatment period will be needed for effective treatment. To determine if the patient is cured a follow-up period of another 12 weeks may be required to ensure that the nail fungus has been adequately treated. Relapse of the disease may require another cycle of treatment.

The amount of the composition that will be used to treat the nail will be enough to fully cover the nail and will include a therapeutically-effective amount of the active. In a composition which contains as an active butenafine hydrochloride, the concentration of the material will generally be about 0.5–15% by weight. Such concentrations will deliver an amount that exceeds minimal inhibitory concentration (MIC) for the targeted organism. As mentioned previously, it is preferred that the composition be applied to the nail and then covered for the entire period of time during which the nail is being treated. This may be covered in a manner previously discussed or an additional nail lacquer or press-on nail may be used to retain the composition in place. A nail lacquer using an acrylate or methacrylate base as the polymerizing material is particularly useful. This may be applied similarly to a nail polish to ensure that a high lacquer finish covers the gel composition. This is particularly useful when the gel composition has a film former that forms a film on the exposed surface of the gel after application to the nail. Thus, the nail lacquer will provide a covering and the covering can be occlusive or semi-occlusive.

In general a subject is determined to have onychomycosis of the nail under consideration if there is a nail with a positive KOH at screening or a mycologic culture positive for a dermatophyte or other characteristics.

A successful treatment in the clinic generally means that there is mycological cure (e.g., no fungal growth) with at least >3 mm nail growth at 28 weeks after completion of a treatment regimen.

Another aspect of the invention pertains to the use of the antifungal compound for the preparation of a topical composition for the treatment of a nail fungal disease. As noted above, a therapeutically-effective amount of this topical composition is (a) applied to the surface of the nail to be treated, (b) maintained on the nail for up to about 24 hours (preferably about 4 to about 12 hours), and (c) removed for a short time, preferably for about 4 to about 12 hours. Steps (a) through (c) are the repeated until the fungal disease has been successfully treated.

Article of Manufacture

Another aspect of this invention is an article of manufacture that comprises the combination of the composition as discussed hereinbefore held in a suitable container for dispensing the composition along with instructions for using the composition in accordance with the method of treatment. It is well known that before a new pharmaceutical composition can be sold in the United States, it must obtain approval from the Food and Drug Administration. The approval process is the approval of the composition itself and also the labeling instructions which are to accompany the composition. These labeling instructions generally provide the instructions for the use of the composition. Thus, an important aspect of this invention is the article of manufacture which will ultimately be sold to the consumer who is either predisposed to an antifungal condition such as onychomycosis or is infected with a fungal infection. The container that is useful for the topically applied gel of this invention is any suitable container that holds the composition for the period of time sufficient for performing at least part of the treatment regimen. Thus, the container may be a tube which is flexible and squeezable having an orifice through which the gel is squeezed for application to the nail. Alternatively, a container may simply be a standard glass, plastic or metal container which is of course nonreactive with the material. That which is designed to easily deliver the composition either by having a flat stick or brush for applying or dabbing the composition to the nail surface. The labeling instructions which are associated with the container and which may actually be attached to the container, or preferably are simply associated with it, provide the instructions for the use of the composition. Thus, the instructions will describe the regimen for treatment to the consumer and the physician. These written instructions will be consistent with the method of treatment discussed hereinbefore in this application. Additional considerations for the type of container may include a tube having a nasal tip on it which often is used for ophthalmic formulations. But generally, if a narrowed orifice is used, such as a nasal tip tube, the tube will be squeezable so that the composition of the invention can be squeezed directly onto the surface to be treated.

The following Examples serve to illustrate the invention. They are representative in nature and should not be construed in any way as narrowing or limiting the scope of the invention.

EXAMPLE 1

A gel having the following composition was prepared.

| Ingredients | Wt % |
| --- | --- |
| Water | 19.86 |
| Propylene glycol | 10 |
| Hydroxypropylcellulose | 2 |
| Ethanol | 50 |
| Polyolprepolymer-2 | 1 |
| Sodium laureth sulfate | 3 |
| Benzyl alcohol | 1 |
| Lactic acid | 0.58 |
| Sodium lactate | 9.36 |
| Povidone K-90 (PVP K-90) | 0.20 |
| Butenafine hydrochloride | 3 |

The water, propylene glycol, and a portion of the ethanol were mixed until uniform. The hydroxypropyl cellulose was then added and mixed until hydrated, followed by addition of the surfactant and further mixing until uniform. To the remainder of the ethanol in a separate vessel was added sequentially with stirring PVP K-90, polyolprepolymer-2, benzyl alcohol, and butenafine hydrochloride until solution was achieved. This solution was then added to the hydroxypropyl cellulose solution and stirred until uniform. Lactic acid (88%) and sodium lactate (60%) were then added and mixing continued until uniform. If necessary, additional ethanol was added to achieve the target batch size.

EXAMPLE 2

This Example provides a screening method to determine whether an antifungal agent penetrates a human nail.

Human toenails were stratified in such a way that each formulation to be tested was employed on nails from three different donors. A dose of 7.0 μl of a test gel formulation containing labeled $^{14}C$ butenafine was applied over a 0.36 cm$^2$ marked area on the nail. The dose was dispensed slowly, allowing each semi-drop to dry before adding more of the dose to the nail. After dosing, the treated nail was allowed to dry for a further 15 minutes. The dosed nail along with the underlying skin was pressed on agar to ensure contact of the nail to the skin and the skin to an agar. The agar plate was then covered with saran wrap, leaving a hole such that the nail was exposed to the air. After 24 hours, the nail, nail wash, skin, and agar beneath the nail were collected and analyzed, using a liquid scintillation counter.

It was found that the concentration of butenafine delivered to the nail bed far exceeded the minimum inhibitory concentration needed for successful treatment of fungal diseases.

EXAMPLE 3

This example describes a treatment regimen for using compositions of this invention to treat onychomycosis.

The objective of the study was to compare the safety and efficacy of 5% and 8% by wt. butenafine hydrochloride composition of this invention when used topically once daily with or without occlusion to treat distal subungual onychomycosis of the toenail caused by dermatophyte infection.

Eighty (80) subjects were enrolled in a multicenter, parallel, randomized, double-blind trial of butenafine hydrochloride 8% and 5% composition (see Tables D and E) with and without occlusion. Subjects with distal subungual onychomycosis of the toenail, diagnosis confirmed by KOH and culture, applied the assigned medications once daily (overnight) for 24 weeks. Of the 79 subjects who were evaluated for efficacy, 27 received 8% butenafine nail product with occlusion, 27 received 5% butenafine nail product with occlusion, and 26 received 5% butenafine nail product without occlusion. The three groups were demographically and clinically similar. Four primary efficacy endpoints, Culture Negative, Responder (Investigator Global Assessment of "Moderately Improved" or better), Clinical Cure (Negative Culture plus Responder), and Alternate Cure (Negative culture plus ≧3 mm increase in UTNPL from Baseline) were assessed. The study shows trends and numerical differences in the subjects treated. All subjects with post-baseline cultures showed conversion to negative culture after therapy. Additionally, the Responder, Clinical, and Alternate Cure rates were higher in the 8% butenafine nail product group than in 5% butenafine groups with or without occlusion. All regimens are therapeutically useful.

The results are shown in the following table.

TABLE F

| Subject Outcome Category | Week 28 (4 Week Follow-Up) | | |
|---|---|---|---|
| | 8% occluded | 5% occluded | 5% non-occluded |
| Culture Negative | 100% (26/26) | 100% (26/26) | 100% (24/24) |
| Responder | 42% (11/26) | 33% (9/27) | 40% (10/25) |
| Clinical Cure | 42% (11/26) | 33% (9/27) | 40% (10/25) |
| Alternate Cure | 46% (12/26) | 41% (11/27) | 30% (7/23) |

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A topical antifungal composition for treating a nail fungal disease in a mammal, which composition comprises:
   (a) about 1% by weight to about 10% by weight of an antifungal compound, or a pharmaceutically acceptable salt thereof, wherein the antifungal compound is represented by the formula

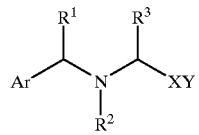

wherein: $R^1$, $R^2$, and $R^3$ are independently hydrogen or lower alkyl; X is —$(CH_2)_n$— in which n is 0, 1 or 2; Y is aryl or heteroaryl; and Ar is aryl or heteroaryl; and
   (b) about 30% by weight to about 70% by weight of a pharmaceutically-acceptable solvent,
   (c) about 0.5% by weight to about 15% by weight of a gelling agent,
   (d) about 0.5% by weight to about 10% by weight of an adhesion-promoting agent,
   (e) about 0.1% by weight to about 3% by weight of a film-forming agent,
   (f) about 0.5% by weight to about 5% by weight of a surfactant,
   (g) about 0% by weight to about 20% by weight of a keratolytic agent, and
   (h) water in an amount sufficient to bring the composition to 100%; wherein said composition is capable of adhering to the surface of a human nail and delivering the antifungal compound through the nail barrier.

2. The composition of claim 1, wherein the antifungal compound is butenafine or a pharmaceutically acceptable salt of the compound.

3. The composition of claim 1, wherein the antifungal compound is butenafine hydrochloride.

4. The composition of claim 1, wherein the composition is aqueous.

5. The composition of claim 1, wherein the pH is adjusted to about 3.0 to about 8.0.

6. A method of treating a nail fungal disease in a human, which method comprises (a) applying a therapeutically-effective amount of a topical antifungal gel composition to the surface of the nail to be treated,
(b) maintaining the composition on the nail for at least about 4 hours to about 12 hours,
(c) removing the composition from the nail for about 4 to 12 hours, and
(d) repeating steps (a) through (c) until the nail fungal disease has been successfully treated, wherein the composition comprises
  (i) about 1% by weight to about 10% by weight of an antifungal compound represented by the formula

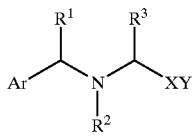

wherein: $R^1$, $R^2$, and $R^3$ are independently hydrogen or lower alkyl; X is —$(CH_2)_n$— in which n is 0, 1 or 2; Y is aryl or heteroaryl; and Ar is aryl or heteroaryl and
  (ii) about 30% by weight to about 70% by weight of a pharmaceutically-acceptable solvent,
  (iii) about 0.5% by weight to about 15% by weight of a gelling agent,
  (iv) about 0.5% by weight to about 10% by weight of an adhesion-promoting agent,
  (v) about 0.1% by weight to about 3% by weight of a film-forming agent,
  (vi) about 0.5% by weight to about 5% by weight of a surfactant,
  (vii) about 0% by weight to about 20% by weight of a keratolytic agent, and
  (viii) water in an amount sufficient to bring the composition to 100%; wherein said composition is capable of adhering to the surface of the nail to deliver the antifungal compound through the nail barrier.

7. The method of claim 6, wherein steps (a)–(c) are repeated for a period of at least 12 weeks.

8. The method of claim 7, wherein steps (a)–(c) are repeated for a period of at least 24 weeks.

9. The method of claim 6, wherein in step (b) after the composition has been applied to the nail, the composition is maintained on the nail by covering the composition on the nail for the indicated period of time.

10. The method of claim 6, wherein the antifungal compound is butenafine or a pharmaceutically acceptable salt of the compound.

11. The method of claim 9, wherein the antifungal compound is butenafine hydrochloride.

12. The method of claim 6, wherein the composition is aqueous.

13. The method of claim 12, wherein the pH is adjusted about 3.0 to about 8.0.

14. An article of manufacture which comprises the combination of the composition of claim 1 with a device that is designed to be placed over the nail of a subject to retain the composition on the nail of the subject after the composition is applied to the nail.

15. The article of manufacture of claim 14, wherein the device is designed to have an impervious backing sheet which defines a recessed area sufficient to retain an effective amount of the composition of claim 1 within the recessed area, said device further having adhesive means to attach the recessed area over the composition to hold it on the nail of the mammal being treated.

16. An article of manufacture for treating nail fungal infections in mammals, which article of manufacture comprises a container containing the composition of claim 1 in combination with printed labeling instructions describing the method of treating nail flngal infections in accordance with the method of claim 6.

17. The composition of claim 1, wherein the gelling agent is a gum, resin, polyacrylamide, mitrocellulose or cellulose derivative.

18. The composition of claim 17, wherein the gelling agent is hydroxypropylcellulose.

19. The composition of claim 1, wherein the adhesion-promoting agent is a polyurethane compound having the formula:

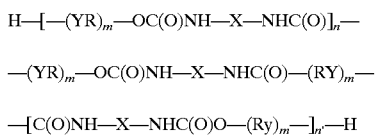

wherein:

X is an alkylene or alkenylene radical containing from 1 to about 20 carbon atoms, or a cycloalkylene or cycloalkenylene radical containing from about 5 to 20 carbon atoms, or a mononuclear or fused ring arylene radical containing from about 6 to about 10 carbon atoms, unsubstituted or substituted with one or more lower alkyl, lower alkoxy, lower alkoxy-substituted lower alkyl, nitro or amino groups or halogen atoms;

Y is oxygen, sulfur, silicon, or —NH—;

each R is the same or different, and is chosen from alkylene, alkenylene, —$SiR^2R^3$—, and —$CR^2R^3$—$NR^4$—$CR^2R^3$—, wherein $R^2$, $R^3$ and $R^4$ are independently hydrogen or lower alkyl;

m is an integer selected to provide a (YR) moiety having a molecular weight of from about 40 to about 6,000; and n and n' are the same or a different integer from 0–30 inclusive, correlated with m so as to provide a polyurethane compound having a molecular weight of up to about 200,000.

20. The composition of claim 19, wherein X is 4,4'-dicyclohexylmethane, Y is oxygen, R is 1,2-propylene, m is 1–4, n and n' are both 12.

21. The composition of claim 1, wherein the film-forming agent is povidone (1-ethyenyl-2-pyrrolidone polymers), polyvinyl alcohol, polyvinyl acetate, polyvinylethyl ether, polyvinylstearyl ether, vinylpyrrolidone/vinylacetate copolymers or nitrocellulose.

22. The composition of claim 21, wherein the film-forming agent is povidone.

* * * * *